US008795592B2

(12) United States Patent
Eiriksson

(10) Patent No.: US 8,795,592 B2
(45) Date of Patent: Aug. 5, 2014

(54) SAMPLE THERMAL CYCLING

(75) Inventor: Ari Eiriksson, South Hamilton, MA (US)

(73) Assignee: Analogic Corporation, Peabody, MA (US)

( * ) Notice: Subject to any disclaimer, the term of this patent is extended or adjusted under 35 U.S.C. 154(b) by 796 days.

(21) Appl. No.: 12/888,818

(22) Filed: Sep. 23, 2010

(65) Prior Publication Data

US 2012/0077197 A1 Mar. 29, 2012

(51) Int. Cl.

| | |
|---|---|
| ***G01N 33/00*** | (2006.01) |
| ***B01L 9/06*** | (2006.01) |
| ***C12M 1/38*** | (2006.01) |
| ***C12M 3/00*** | (2006.01) |
| *C12M 1/36* | (2006.01) |

(52) U.S. Cl.
USPC ....... 422/62; 422/562; 435/286.6; 435/288.4; 435/303.1

(58) Field of Classification Search
USPC .......................................... 422/62; 435/286.6
See application file for complete search history.

(56) References Cited

U.S. PATENT DOCUMENTS

| | | | | |
|---|---|---|---|---|
| 5,302,347 | A | 4/1994 | Van Den Berg et al. | |
| 6,180,372 | B1 | 1/2001 | Franzen | |
| 6,428,987 | B2 | 8/2002 | Franzen | |
| 6,524,830 | B2 * | 2/2003 | Kopf-Sill | 435/91.2 |
| 6,586,233 | B2 | 7/2003 | Benett et al. | |
| 6,613,560 | B1 | 9/2003 | Tso et al. | |
| 6,893,863 | B2 | 5/2005 | Benett et al. | |
| 7,060,948 | B2 | 6/2006 | Cho et al. | |
| 7,537,917 | B2 | 5/2009 | Collins | |
| 7,569,366 | B2 | 8/2009 | Tsukada | |
| 7,645,070 | B2 | 1/2010 | Atwood et al. | |
| 2005/0153296 | A1 * | 7/2005 | Berlin | 435/6 |
| 2008/0038163 | A1 * | 2/2008 | Boege et al. | 422/188 |

* cited by examiner

*Primary Examiner* — Jill Warden
*Assistant Examiner* — Brittany Fisher
(74) *Attorney, Agent, or Firm* — Driggs, Hogg, Daugherty & Del Zoppo Co., LPA; Anthony M. Del Zoppo, III

(57) ABSTRACT

A sample processing apparatus includes a sample carrier receiving region configured to receive sample carrier carrying one or more samples for processing by the sample processing apparatus, and a thermal control system that controls a thermal cycling of the one or more samples for processing by the sample processing apparatus by selectively varying a pressure over a fluid in substantial thermal communication with the sample carrier, thereby varying a boiling point temperature of the fluid.

31 Claims, 7 Drawing Sheets

SAMPLE THERMAL CYCLING

TECHNICAL FIELD

The following generally relates to thermal cycling a sample in connection with processing the sample and is described with particular application to DNA processing such as DNA sequencing; however, the following is also amenable to other DNA processing and/or processing of other samples.

BACKGROUND

Micro channel devices include, but are not limited to, devices which carry a small volume of a sample for processing and/or analysis. Micro channel devices have been used in biochips, labs-on-a-chip, inkjet printheads, and other micro based technologies. In some instances, a temperature of a sample in a micro channel of a micro channel device is controlled so that it is within a predetermined temperature range for processing, analysis, and/or other purposes. Controlling the temperature includes heating and/or cooling the sample at a predetermined rate so that the temperature of the sample is maintained within a predetermined temperature range or cycled between two or more predetermined temperature ranges.

One technique for heating and/or cooling the fluid involves using a Peltier device, which, generally, is a thermoelectric heat pump that transfers heat from one side of the Peltier device to the other side of the Peltier device. With this technique, the Peltier device is placed in thermal contact with the micro channel device, and an appropriate voltage is applied to the Peltier device to create a temperature gradient for transferring heat between the sides of the Peltier device, either away from or towards the micro channel device. The polarity of the applied voltage determines whether the Peltier device heats up or cools down the micro channel device and thus the sample. A foil heater likewise has been placed in thermal contact with the micro channel device.

Unfortunately, a Peltier device (or the like) generally requires good mechanical/thermal contact between the Peltier device and the micro channel device. Such contact may require accurate and precise mechanical alignment and pressure, which may not be readily achieved. Moreover, heat transfer via the Peltier device may be non-uniform through conduction through the side of the Peltier device in mechanical contact with the micro channel device as well controlled thermal conductance can be difficult to achieve.

Furthermore, using such a device may increase the thermal mass that participates in thermal cycling, which may increase the power required to implement thermal cycling. As a consequence, using a Peltier or similar device may increase the overall size of the micro channel device, power consumption and/or dissipation of the micro channel device, and/or the cost of the micro channel device, as well as provide non-uniform and/or relatively slow temperature control. Moreover, the performance of a Peltier devices may degrade over time, for example, due to mechanical damage to the Peltier sub-elements caused by thermal cycling. This can result in non-uniform temperatures across the surfaces of the Peltier device, which can cause undesirable temperature variations within the micro channel device.

SUMMARY

Aspects of the application address the above matters, and others.

In one aspect, a sample processing apparatus includes a sample carrier receiving region configured to receive sample carrier carrying one or more samples for processing by the sample processing apparatus, and a thermal control system that controls thermal cycling of the one or more samples for processing by the sample processing apparatus by selectively varying the pressure over a fluid in substantial thermal communication with the sample carrier, thereby varying the boiling point temperature of the fluid. Heat may be added to the fluid and sample carrier using a light source, resistive heating and/or other conventional means, while cooling and temperature control of the fluid and sample carrier can be achieved primarily by adjusting the pressure over the fluid and causing boiling of the fluid at the desired fluid temperature.

In another aspect, a method includes setting a boiling point temperature of a fluid in substantial thermal communication with a sample carrier carrying a sample to be processed by applying a pressure over the fluid that corresponds to a predetermined target temperature for the sample and boiling the fluid, wherein heat transfers between the boiling fluid and the sample, thereby bringing or maintaining a temperature of the sample at the target temperature.

In another aspect, a system for processing samples includes means for supporting a sample carrier carrying a sample and means for thermocycling the sample carried by the sample carrier based on a varying a pressure of a fluid in substantial thermal communication with the sample carrier.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
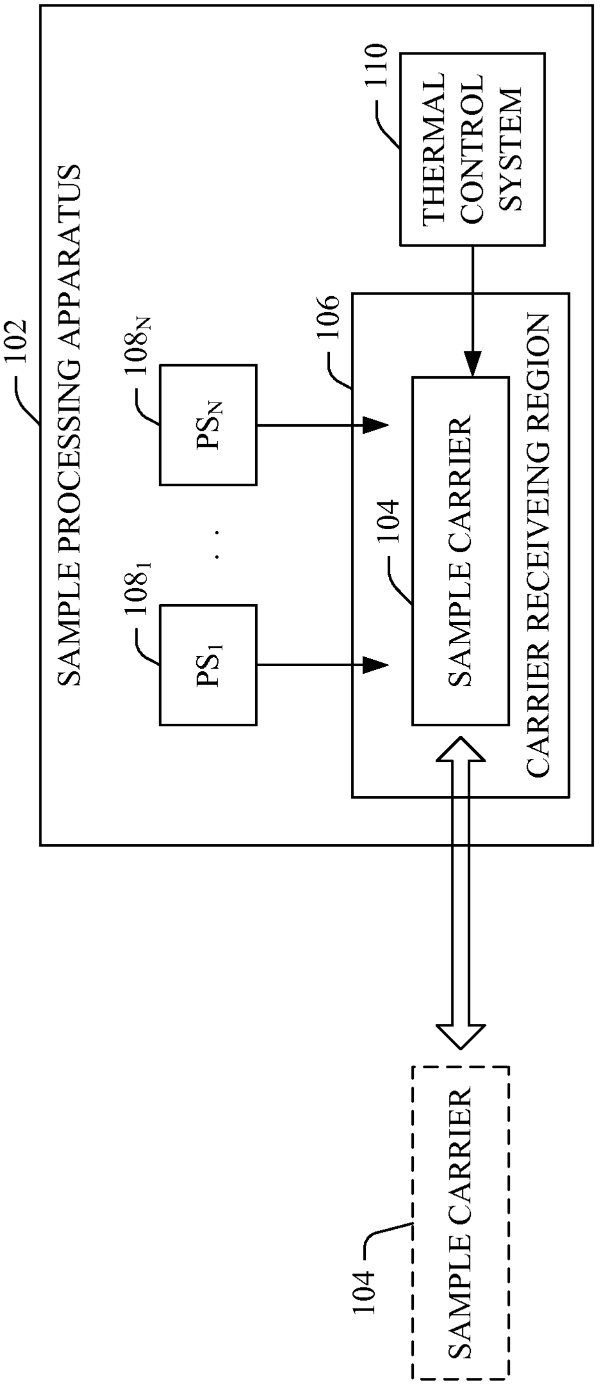
FIG. 1 illustrates an example sample processing apparatus.

FIG. 1 illustrates a sample processing apparatus 102 for processing, in parallel or in series, one or more samples located on a micro channel device such as a sample carrier 104. A non-limiting example of a suitable sample carrier is a biochip with one or more micro channels for bio-samples (e.g., blood, saliva, skin cells, etc.). In this instance, the sample processing apparatus 102 may be configured for DNA (e.g., sequencing), enzymatic, protein, and/or other processing and/or analysis. Other suitable carriers include, but are not limited to, a micro-channel device, a lab-on-a-chip, and/or other sample carrier.

The sample processing apparatus 102 includes a carrier receiving region 106 that is configured to receive the sample carrier 104. The carrier receiving region 106 supports a loaded carrier 104 for processing by the sample processing apparatus 102. The sample processing apparatus 102 further includes one or more processing stations ($PS_1$, . . . $PS_N$)

$108_1, \ldots, 108_N$ (wherein N is an integer equal to or greater than one), collectively referred to herein as processing stations 108, that process one or more samples of the sample carrier 104 loaded in the sample carrier receiving region 106.

In the context of processing samples including DNA, the illustrated processing stations 108 are configured to carry out at least one or more of the following: extraction/purification of DNA fragments from the sample, fragment labeling, fragment replication, and fragment separation (e.g., through electrophoresis). Replication generally is achieved through polymerase chain reaction (PCR) which includes thermal cycling the bio-sample between various temperatures between zero (0) degrees Celsius (° C.) and 100° C., such as between 56° C., 72° C., and/or 92° C., and/or other temperatures. In this context, the sample processing apparatus 102 includes a DNA analyzer, sequencer, and/or other processor.

The sample processing apparatus 102 also includes a thermal control system 110 that controls a temperature cycling of the sample carrier 104, thereby controlling a temperature cycling of the one or more samples carried by the sample carrier 104. The illustrated thermal control system 110 controls the temperature cycling of the sample carrier 104 by varying a pressure over a fluid that is in substantial thermal communication with the sample carrier 104. The thermal control system 110 includes a heat source such as a radiating, resistive, self-heating and/or other heating source.

As described in greater detail below, in one instance, the thermal control system 110 is configured to apply a pressure over the fluid so that a boiling point temperature of the fluid corresponds to a predetermined target temperature for the sample. Generally, as the pressure and the boiling point temperature for a fluid are proportional, increasing the pressure increases the boiling point, and decreasing the pressure decreases the boiling point. The fluid is then boiled and heat transfers between the boiling fluid and the sample, which either increases or decreases the temperature of the sample.

Using a boiling fluid allows for increasing sample temperature very rapidly with built-in protection against overheating since excess heat generally will cause additional boiling with no to minimal temperature increase and decreasing sample temperature very rapidly since the fluid self-cools by partial boiling when its pressure is reduced. This approach also allows for maintaining a substantially uniform temperature between samples since pressures can be kept about equal in the fluid volumes and for mitigating relying on good uniform physical contact with an external thermal cycling device.

Figure 2:
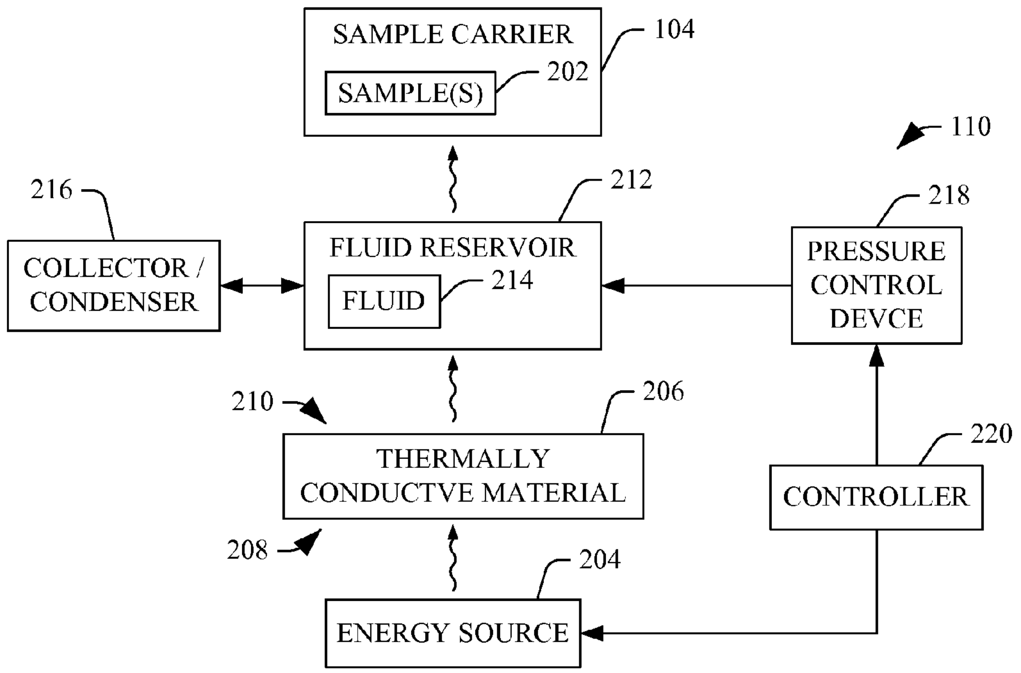
FIGS. 2-5 illustrate examples of a thermal control system of the sample processing apparatus.

FIG. 2 illustrates an example of a suitable thermal control system 110 in connection with a sample carrier 104 carrying one or more samples 202 to be processed by the sample processing apparatus 102.

An energy source 204 is used to supply energy for thermal cycling. The illustrated source 204 is configured to supply one or more different levels of energy in accordance with one or more different target temperatures for thermal cycling of the sample(s) 202, including, in one instance, supplying no energy to facilitate decreasing the temperature of the sample(s) 202. The illustrated source 204 radiates energy. Examples of suitable source include, but are not limited to, infrared lamp, a visible light lamp, a resistor, microwave source and/or other source of energy or a combination of two or more energy sources.

A thermally conductive material 206 is disposed in connection with the heat source 204 so as to receive the energy supplied by the heat source 204. The thermally conductive material 206 absorbs the energy on a side 208, which faces the supplied energy, and transfers heat to an opposing side 210 of the material 206 facing away from the source 204. In one instance, the thermally conductive material 206 substantially absorbs energy, which mitigates energy such as radiant energy directly striking the one or more samples 202. This may provide overheat protection for the one or more samples 202, as further discussed below.

A suitable thermally conductive structure of material 206 will have sufficient fluid and vapor flow passages, as to allow vapor bubbles which form on the surfaces of material 206 during fluid boiling to rise upward towards the fluid surface. This may mitigate trapping vapor bubbles within and/or under suitable thermally conductive structure 206, where the vapor bubbles can compromise the heat transfer and temperature uniformity by forming large vapor pockets.

Examples of suitable thermally conductive materials include aluminum (such as aluminum anodized to facilitate absorption of IR or visible light radiation), copper and alumina ceramics. The thermally conductive material 206 can be placed in substantial thermal communication with the fluid and/or the one or more samples 202, which may improve heat transfer therebetween. In addition, the structure of material 206 may incorporate fins, sponges and/or other well known methods to increase the surface area of the material 206.

A fluid reservoir 212 is configured to hold a fluid 214. The fluid reservoir 212 and hence the fluid 214 is in substantial thermal communication with the thermally conductive material 206 (e.g., the opposing side 210) and with the sample carrier 104. The fluid 214 facilitates transferring heat to and/or from the one or more samples 202 carried by the sample carrier 104. For explanatory purposes, the fluid reservoir 212 is shown separated from both the thermally conductive material 206 and the sample carrier 104 by respective gaps. However, the fluid reservoir 212 may alternatively be in physical contact with one or both of the thermally conductive material 206 and the sample carrier 104. Examples of suitable fluids include, but are not limited to ammonia, water, $C_5H_{12}$, $C_3H_8$, and/or other single compound fluids. A fluid or fluids made from multiple compounds (such as the refrigerant R-410, which is a mixture of 3 compounds) can also be used.

Fluids with high vapor pressures in the desired temperature control range generally have small variations in boiling temperature for a given change in pressure, which may improve the accuracy of the temperature control for a given accuracy in the pressure control. High vapor pressures also may allow more rapid mass flow of vapor to and from the fluid reservoir for a given flow cross section and available pressure differential to drive the vapor flow. Fluids with low vapor pressures have lower maximum pressure and therefore may require less structural strength of the fluid reservoir than fluids with high vapor pressures. One person skilled in the relevant art will understand the nature of these fluids and appreciate that the choice of the fluid may be a compromise between performance and cost factors.

A collector/condenser 216 collects vaporized fluid from the fluid reservoir 212 during boiling of the fluid. The collector/condenser 216 condenses the collected vapor into the fluid and returns the condensed fluid to the fluid reservoir 212. The collector/condenser 216 may include a Micro Electro Mechanical Systems (MEMS) based collector and/or condenser, and/or other micro technology based components.

A pressure control device 218 determines a pressure over the fluid 214 in the fluid reservoir 212, thereby determining a boiling point of the fluid 214. The illustrated pressure control device 218 can be controlled so as to vary the pressure over the fluid 214 to change the boiling point of the fluid 214, for example, depending on whether heat is to be transferred to the sample(s) 202 or away from the sample(s) 202. The pressure control device 218 may include components such as a vapor compressor, a pump, a container holding compressed vapor and/or liquid, a chiller, or the like. Such components may be based on MEMS and/or other micro technology.

A controller 220 controls the energy source 204 and the pressure control device 218. Such control of the energy source 204 includes turning the energy source 204 on and off and adjusting an output power of the energy source 204 to facilitate bringing the fluid to a boil. Control of the pressure control device 218 includes conveying a signal indicative of a pre-determined pressure for the fluid 214 to set the boiling point of the fluid.

As discussed herein, the thermally conductive material 206 is placed between the source 204 and the sample carrier 104 and in substantial communication with the fluid reservoir 212. In this configuration, the thermally conductive material 206 substantially absorbs the energy from the source 204, which, in the case of radiant energy, may reduce or mitigate energy from striking the samples 202. Instead, the thermally conductive material 206 transfers the energy to the fluid 214, which boils the fluid 214, and the boiling fluid is used to transfer heat with the samples 202.

As such, a maximum temperature exposure of the samples is the boiling point temperature of the fluid 214, and the thermally conductive material 206 can be considered as providing overheat protection. Without the thermally conductive material 206, radiant energy can traverse through the fluid reservoir 212 and strike the samples 202, and raise the temperature of the samples 202 to a temperature greater than boiling point temperature of the fluid 214, which may be too high of a temperature for the processing being performed.

In FIG. 2, the thermal control system 110 is shown external from the sample carrier 104. However, it is to be appreciated that in another embodiment one of more components of the thermal control system 110 can be part of the sample carrier 104. For example, the fluid reservoir 212 and/or the thermally conductive material 206 may be part of the sample carrier 104. In this instance, the pressure control device 218 may interface with the sample carrier 104 via one or more channels for supplying pressure and/or routing vapor and/or fluid. Moreover, the relative size, shape, orientation, geometry, etc. of the components are for explanatory purpose and are not limiting.

Variations are contemplated.

In FIG. 2, the thermally conductive material 206 is disposed between the energy source 204 and the fluid reservoir 212. In another embodiment, the thermally conductive material 206 is disposed between the sample carrier 104 and the fluid reservoir 212. In this instance, the energy source 204 supplies energy directly to the fluid reservoir 212, and heat transfers from the fluid reservoir 212 to the thermally conductive material 206 to the one or more samples 202.

In yet another embodiment, the system 110 includes multiple thermally conductive materials 206, with at least one thermally conductive material 206 disposed between the energy source 204 and the fluid reservoir 212 (as shown in FIG. 2) and another thermally conductive material 206 disposed between the sample carrier 104 and the fluid reservoir 212.

In yet another embodiment, the thermally conductive materials 206 is omitted.

Figure 3:
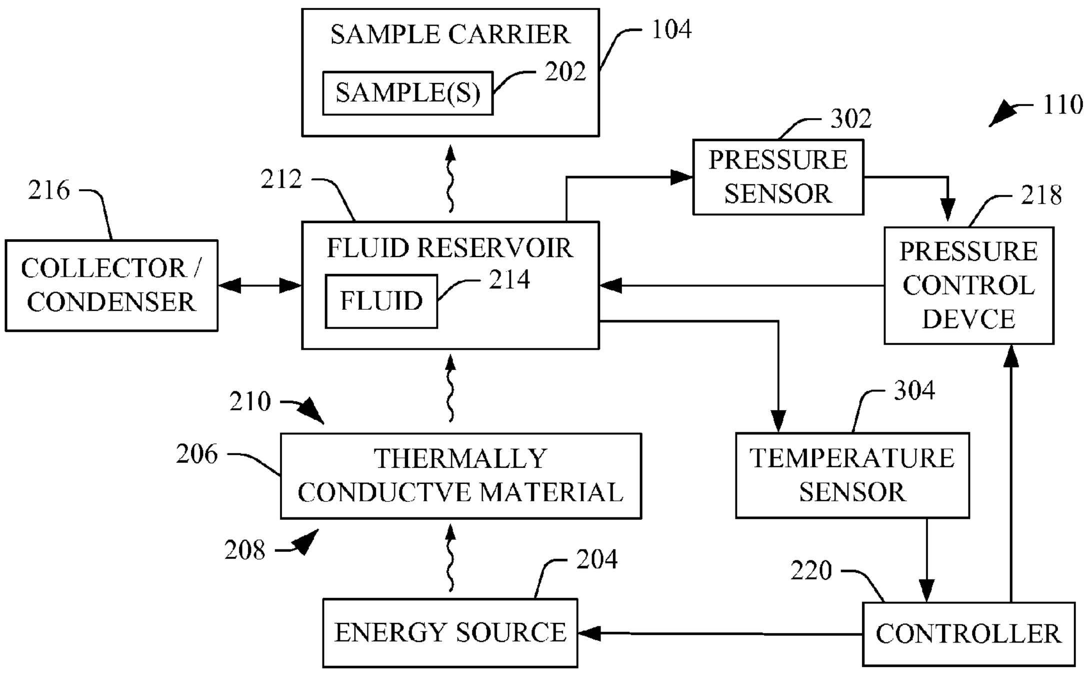

FIG. 3 illustrates an embodiment in which the system 110 also includes at least one of a temperature sensor 304 and/or a pressure sensor 302.

The temperature sensor 304 senses a temperature of the fluid 214 and provides a feedback signal indicative of the sensed temperature to the controller 220. Such a signal may be used to vary the output of the energy source 204 and/or the pressure applied to fluid 214, for example, where the sensed temperature does not correspond to the target temperature.

The pressure sensor 302 senses of pressure over the fluid 214 and provides a feedback signal indicative of the sensed pressure to the pressure control device 218. This signal can be use to confirm that the pressure over the fluid 214 is the target pressure and/or determine an adjustment to the applied pressure where the pressure over the fluid 214 is not the target pressure.

Figure 4:
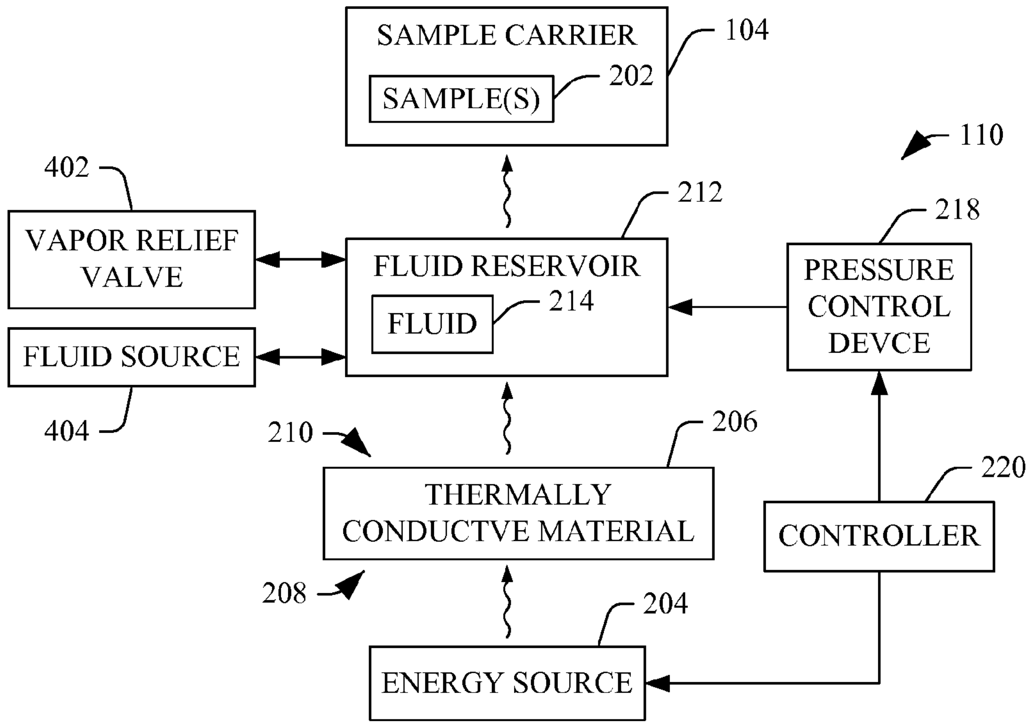

FIG. 4 illustrates an embodiment of the system 110 in which the collector/condenser 216 is replaced with a vapor relief valve 402 and a fluid source 404. In this embodiment, vaporized fluid in the fluid reservoir 212 is released from the system 110 through the vapor relief valve 402, and the fluid source 404 can be used to replenish the fluid in the fluid reservoir 2121 if needed.

Figure 5:
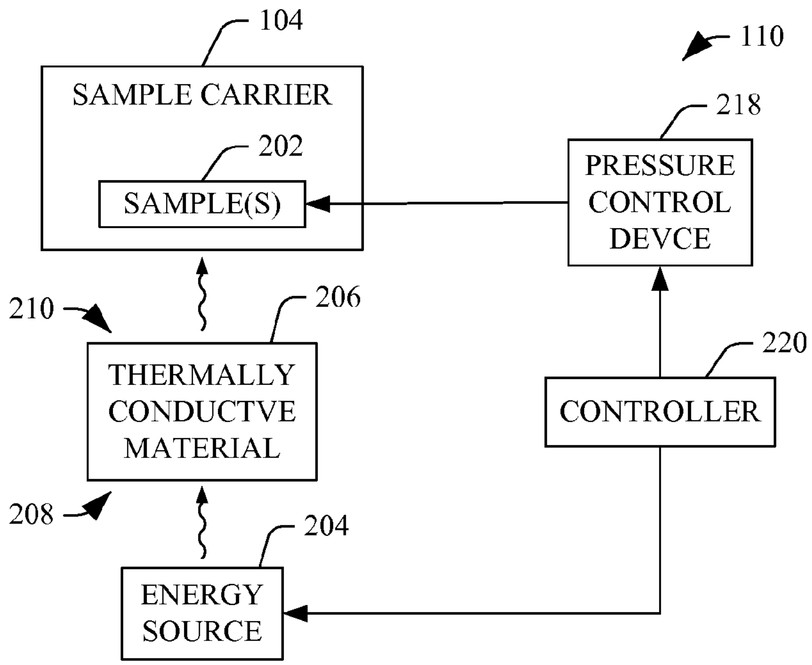

FIG. 5 illustrates an embodiment in which the sample(s) 202 are thermal cycled by applying a pressure over the sample(s) 202 so that a boiling point temperature of the sample(s) 202 corresponds to the target sample temperature, and then boiling the sample(s) 202.

Figure 6:
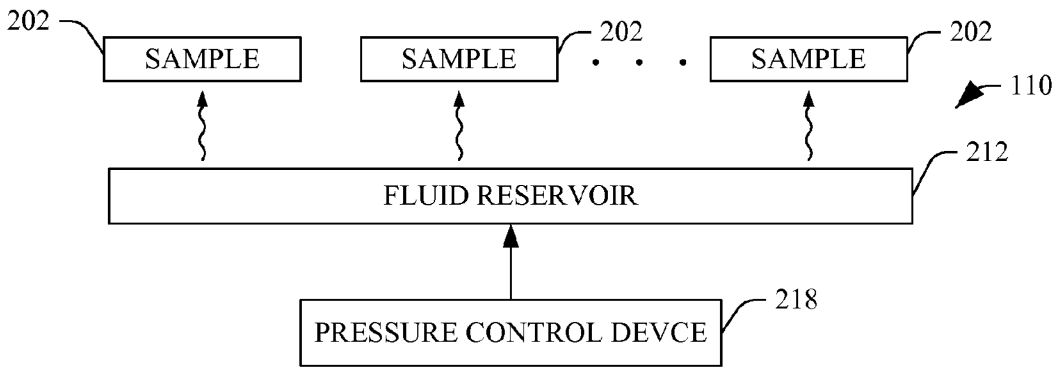
FIGS. 6-8 illustrate examples of thermal control systems in connection with a plurality of samples.
Figure 7:
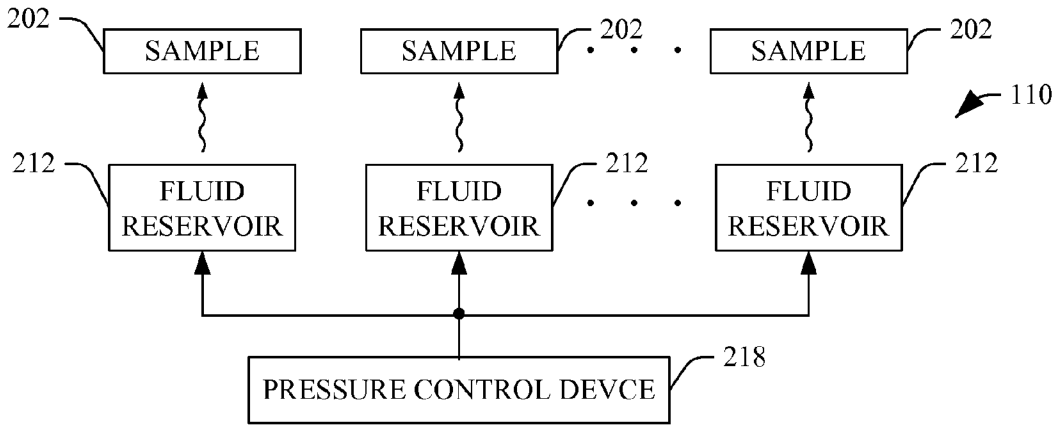
Figure 8:
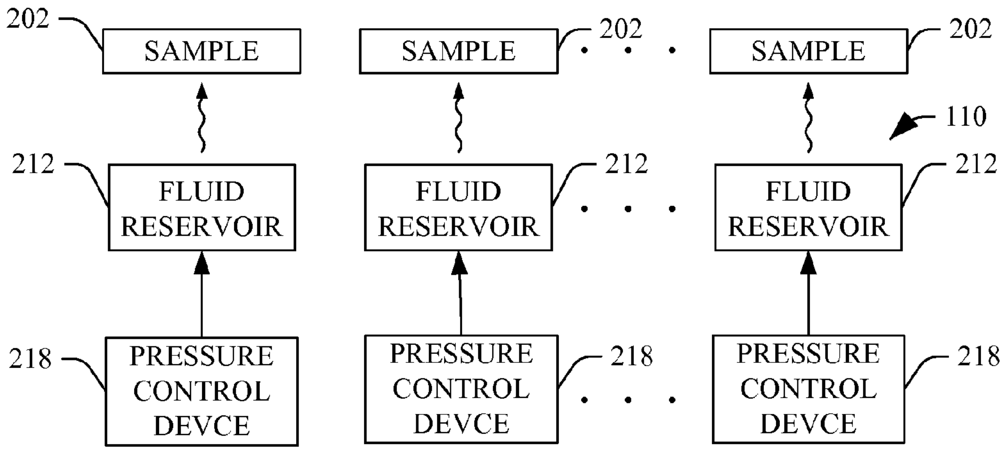

FIGS. 6, 7, and 8 illustrate embodiments showing the thermal control system 110 in connection with multiple samples 202 of the sample carrier 104.

FIG. 6 illustrates an embodiment in which a single pressure control device 218 controls a pressure over the fluid in a single fluid reservoir 212 employed in connection with multiple samples 202.

FIG. 7 illustrates an embodiment in which a single pressure control device 218 individually controls a pressure over the fluid in different fluid reservoirs 212, each reservoir corresponding to a different one of the samples 202.

FIG. 8 illustrates an embodiment in which multiple pressure control devices 218 respectively control a pressure over the fluid in corresponding fluid reservoirs 212 for respective samples 202.

It is to be appreciated that other embodiments, including, but not limited to one or more combinations of FIGS. 6-8, are also contemplated herein.

Figure 9:
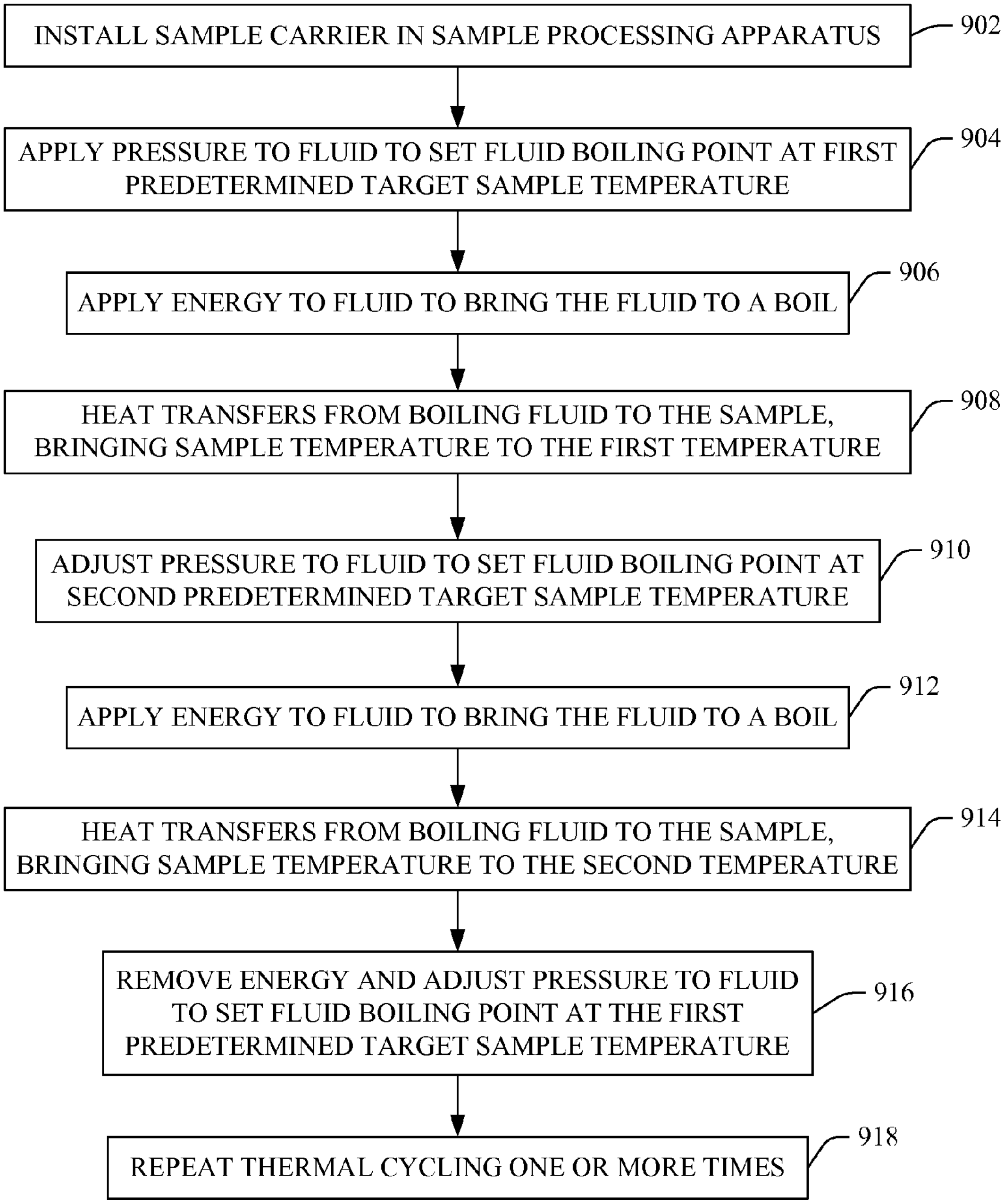
FIG. 9 illustrates a method.

FIG. 9 illustrates a method for cycling a sample temperature between two temperatures. For this example, an initial temperature of the sample is below the two temperatures, and the sample temperature is first brought to the first temperature, and then the temperature of the sample is cycled between the first and second temperatures.

At 902, a sample carrier carrying a sample is installed into a receiving region of a sample processing apparatus.

At 904, a fluid, in thermal communication with the sample in the installed carrier, is placed under pressure so that a first boiling point of the fluid corresponds to a first pre-determined temperature of the thermal cycling.

At 906, a source supplies energy that brings the temperature of the fluid to the first pre-determined temperature. The rate at which the temperature is increased can be set to maximize the boiling heat transfer from the boiling (and rapidly heating) fluid to the sample.

At 908, heat transfers from the fluid to the sample, bringing a temperature of the sample to the first pre-determined temperature.

At 910, after lapse of a first pre-determined time, the pressure is adjusted to set the boiling point of the fluid to a second boiling point, which corresponds to a second pre-determined temperature of the thermal cycling.

At 912, the energy source supplies energy that brings the temperature of the fluid to the second pre-determined temperature.

At 914, heat transfers from the fluid to the sample, bringing the temperature of the sample to the second pre-determined temperature.

At 916, after lapse of a second pre-determined time, the supplied energy is removed from the fluid and the pressure of the fluid is decreased from the second boiling point to the first boiling point. The rate at which the temperature is decreased can be set to maximize the boiling heat transfer from the sample to the boiling (and rapidly cooling) fluid.

At 918, as the temperature of the fluid is within a predetermined range from the first temperature, acts 906-916 can be repeated for one or more thermal cycles.

In the above example, the sample temperature is first raised to a first temperature, and then the sample temperature is cycled between the first temperature and a second higher temperature. In another embodiment, the sample temperature is first lowered to the first temperature. In yet another embodiment, the first temperature may be higher than the second temperature. In yet another embodiment, the temperature of the sample may be cycled through more than two temperatures.

Figure 10:
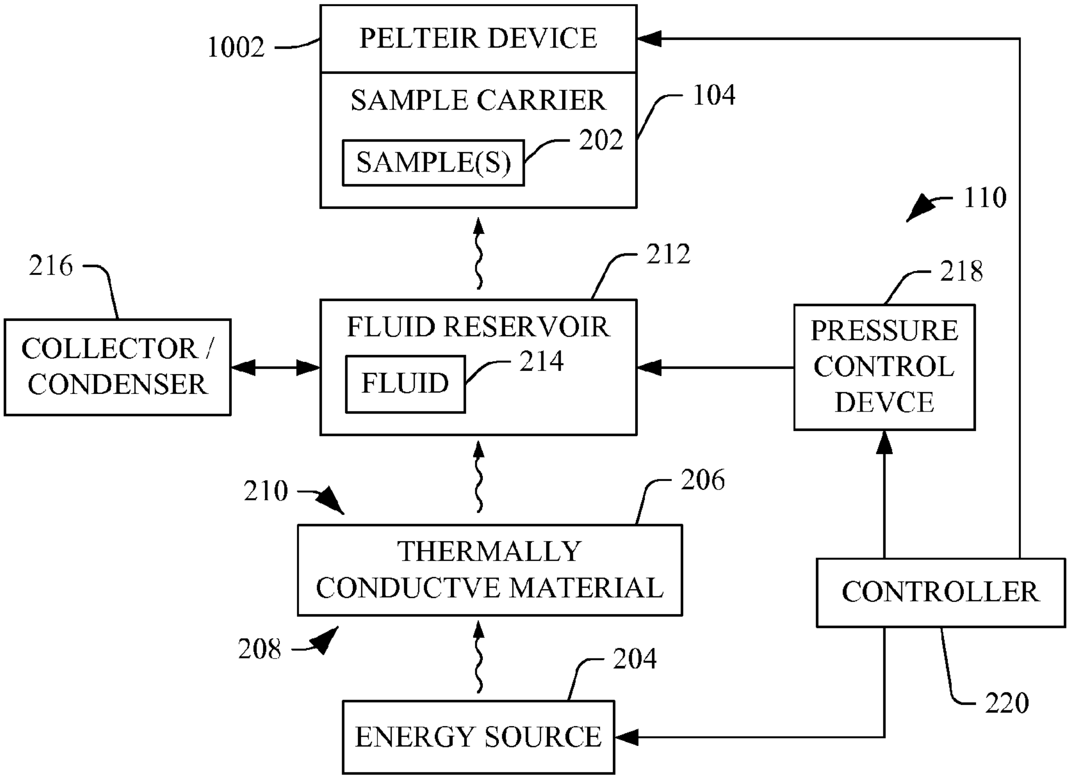
FIGS. 10 and 11 illustrate examples in which thermal control system is used in connection with a Peltier device source.
Figure 11:
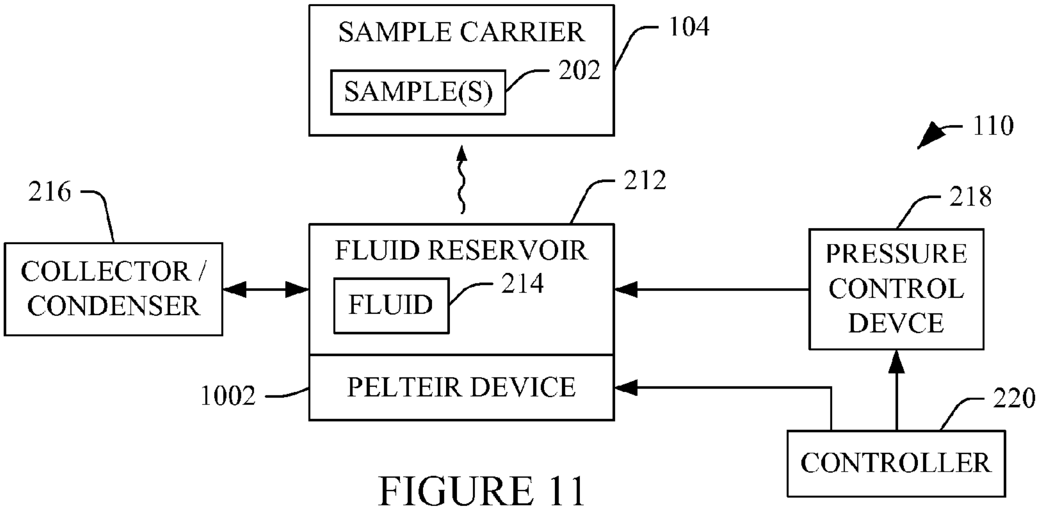

FIG. 10 illustrates an example which is substantially similar to the embodiment of FIG. 2 and additionally includes a Peltier device 1002 that is in thermal communication with the sample carrier 104, which is sandwiched between the fluid reservoir 212 and the Peltier device 1002. In this embodiment, the thermal control system 110 can be used to assist the Peltier device 1002 or the Peltier device 1002 can be used to assist the thermal control system 110. In one instance, this allows for using the Peltier device 1002 for fine tuning, which can be substantially less demanding for the Peltier device 1002 relative to full thermal cycling. As such, the Peltier device 1002 can then be optimized for good thermal uniformity and longer cycle life rather than for high cycling speeds. As shown, the controller 220 can be used to control the Peltier device 1002 as well as the pressure control device 218. FIG. 11 shows a variation in which the energy source 204 includes the Peltier device 1002.

Figure 12:
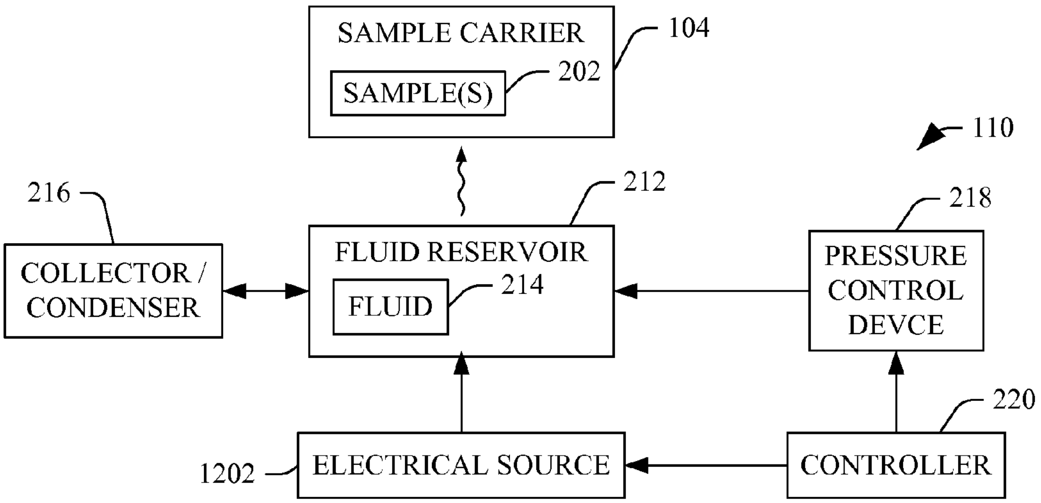
FIG. 12 illustrates an example in which thermal control system is used in connection with an electrical source.

FIG. 12 illustrates an embodiment, which is substantially similar to the embodiment of FIG. 2, in which the energy source 204 includes an electrical (e.g., voltage, current, etc.) source 1202. With this embodiment, a voltage differential can be applied across the fluid 214 to increase the electrical conductivity the fluid 214. As such, the fluid 214 can serve as its own resistive heater (self heating). In one instance, the fluid reservoir 212 would have electrical connections tied into it just like a regular resistive heater would require, and the temperature of the fluid 214 would be limited by the fluid boiling as for the other heating scenarios discussed herein. Additionally or alternatively, one or more chemicals can be added to the fluid 214 to change the electrical conductivity of the fluid 214. As shown, the controller 220 can be used to control the electrical source 1202 as well as the pressure control device 218.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A sample processing apparatus, comprising:

a sample carrier receiving region configured to receive a sample carrier carrying one or more samples for processing by the sample processing apparatus; and a thermal control system that controls a thermal cycling of the one or more samples for processing by the sample processing apparatus—by selectively varying a pressure over a fluid in substantial thermal communication with the sample carrier, the thermal control system including:

a fluid reservoir in substantial thermal communication with the sample carrier, wherein the fluid reservoir holds the fluid;

a pressure control device that varies the pressure over the fluid; and a controller that controls the pressure control device to selectively vary the pressure over the fluid to thermal cycle the one or more samples carried by the sample carrier.

2. The sample processing apparatus of claim 1, wherein the pressure is varied between at least a first pressure that corresponds to a first boiling temperature for the fluid and a second pressure that corresponds to a second boiling temperature for the fluid, wherein the first and second boiling point temperatures are different.

3. The sample processing apparatus of claim 2, wherein the first boiling temperature corresponds to a first target temperature for the one or more samples and the second boiling temperature corresponds to a second target temperature for the one or more samples.

4. The sample processing apparatus of claim 1, wherein the pressure control device determines a boiling point of the fluid in the fluid reservoir.

5. The sample processing apparatus of claim 4, further comprising:

an energy source that supplies energy that brings a temperature of the fluid to the first or second boiling point temperature, wherein the controller controls the energy source to selectively supply different levels of energy.

6. The sample processing apparatus of claim 4, further comprising:

a thermally conductive material disposed between the sample carrier and the fluid reservoir, wherein the thermally conductive material is in substantial thermal contact with the fluid reservoir, thereby exposing the one or more samples to a temperature no higher than the boiling point temperature of the fluid.

7. The sample processing apparatus of claim 3, wherein heat transfers from boiling fluid to the one or more samples, thereby raising temperatures of the one or more samples to one of the target temperatures.

8. The sample processing apparatus of claim 7, wherein heat transfers from the one or more samples to the boiling fluid, thereby lowering the temperatures of the one or more samples to another of the target temperatures.

9. The sample processing apparatus of claim 8, further comprising:

a collector/condenser that collects vaporized fluid, condenses the collected vaporized fluid, and routes the condensed fluid to the fluid reservoir.

10. The sample processing apparatus of claim 8, further comprising:

a vapor relief valve that releases vaporized fluid from the apparatus; and a fluid source that replenishes fluid to the fluid reservoir.

11. The sample processing apparatus of claim 1, wherein a maximum temperature to which the one or more samples is exposed to is a maximum of the fluid boiling point temperature.

12. The sample processing apparatus of claim 4, wherein the fluid reservoir includes a plurality of individual sub-reservoirs respectively in substantial thermal communication with different sample carriers, and the pressure control device varies the pressure over fluid in the plurality of individual sub-reservoirs.

13. The sample processing apparatus of claim 1, wherein the fluid includes the one or more samples.

14. The sample processing apparatus of claim 1, further comprising:

at least one sample processing station, wherein the sample processing station is configured to facilitate replicating DNA fragments through polymerase chain reaction.

15. The sample processing apparatus of claim 1, wherein the sample processing apparatus is a DNA analyzer.

16. The sample processing apparatus of claim 1, further comprising:

a Peltier device in substantial thermal communication with the sample carrier, wherein the thermal control system and the Peltier device are concurrently employed to thermal cycle the one or more samples.

17. The sample processing apparatus of claim 1, further comprising:

an electrical source that applies a voltage across the fluid, wherein the thermal control system and the electrical source are concurrently employed to thermal cycle the one or more samples.

18. The sample processing apparatus of claim 17, wherein the fluid behaves as a heat source and the fluid heats itself.

19. The sample processing apparatus of claim 1, wherein the fluid includes refrigerant R-410.

20. The sample processing apparatus of claim 1, wherein the fluid includes ammonia.

21. The sample processing apparatus of claim 1, wherein the fluid includes water.

22. The sample processing apparatus of claim 1, wherein the fluid includes $C_5H_{12}$, $C_3H_8$.

23. The sample processing apparatus of claim 4, further comprising:

a thermally conductive material disposed between the energy source and the fluid reservoir, wherein the thermally conductive material is in substantial thermal contact with the fluid reservoir, thereby exposing the one or more samples to a temperature no higher than the boiling point temperature of the fluid.

24. A method, comprising:

receiving a sample carrier in a sample carrier receiving region configured to receive the sample carrier, wherein the sample carrier carries one or more sample for processing by a sample processing apparatus; and controlling, with a thermal control system, a thermal cycling of the one or more samples for processing by the sample processing apparatus by selectively varying a pressure over a fluid in substantial thermal communication with the sample carrier, wherein the thermal control system includes a fluid reservoir in substantial thermal communication with the sample carrier and the fluid reservoir holds the fluid, wherein the thermal control system includes a pressure control device that varies the pressure over the fluid, and wherein the thermal control system includes a controller that controls the pressure control device to selectively vary the pressure over the fluid to thermal cycle the one or more samples carried by the sample carrier.

25. The method of claim 24, further comprising:

changing the boiling point temperature of the fluid to a second boiling point temperature by applying a second pressure over the fluid that corresponds to a pre-determined second target temperature for the sample; and boiling the fluid, wherein heat transfers between the boiling fluid and the sample, thereby bringing the temperature of the sample to the second target temperature.

26. The method of claim 25, wherein the second boiling temperature is greater than the first boiling point temperature, and heat transfers from the boiling fluid to the sample.

27. The method of claim 25, wherein the second boiling point temperature is less than the first boiling point temperature, and heat transfers from the sample to the boiling fluid.

28. The method of claim 25, wherein the boiling point temperature is changed for thermocycling the sample for processing.

29. The method of claim 24, wherein a maximum temperature of the sample corresponds to the boiling point temperature of the fluid.

30. The method of claim 24, wherein the sample includes a DNA fragment undergoing DNA analysis.

31. The method of claim 30, wherein the DNA analysis includes replicating the DNA fragment via polymerase chain reaction.

* * * * *